United States Patent
Hirowatari et al.

(10) Patent No.: US 7,262,060 B2
(45) Date of Patent: Aug. 28, 2007

(54) METHOD FOR ASSESSING NICOTINE DEPENDENCE

(75) Inventors: Yuji Hirowatari, Kanagawa-ken (JP); Katsuko Hara, Nara-ken (JP); Hakuo Takahashi, Shiga-ken (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 10/972,337

(22) Filed: Oct. 26, 2004

(65) Prior Publication Data

US 2005/0112771 A1 May 26, 2005

(30) Foreign Application Priority Data

Oct. 27, 2003 (JP) ............................. 2003-365818

(51) Int. Cl.
*G01N 33/00* (2006.01)

(52) U.S. Cl. .................... 436/96; 436/63; 436/901; 546/279.4

(58) Field of Classification Search ............... 436/96, 436/63, 901; 546/279.4
See application file for complete search history.

(56) References Cited

U.S. PATENT DOCUMENTS

2002/0052017 A1    5/2002   Hirowatari et al.

OTHER PUBLICATIONS

Rausch et al. Prog. Neuro-Psychopharmacol. & Biol. Psychiat., vol. 13, 1989, pp. 907-916.*
Netter P et al: "Addictive and nonaddictive smoking as related to responsivity to neurotransmitter systems"; Behavioural Pharmacology, Sep. 2002, vol. 13, No. 5-6; Sep. 2002, pp. 441-449, XP009043607, ISSN: 0955-8810.
Paul A. Robiolio, MD, et al; Corcinoid Heart Disease Correlation of High Serotinia Levels with Valvular Abnormalities Detected by Cardiac Catheterization and Echocardiography; Circulation 1995; 92: 790-795.
Ashwin A. Patkar, et al; Differences in Platelet Serotonin Transporter Sites Between Africian-American Tobacco Smokers and Non-smokers; Psychopharmacology (2003) 166: 221-227.
K. Racke, et al.; Nictine and muscarinic modulation of 5-hydroxytryptamine (5-HT) release from procine and canine small intestine. The Clinical Investigator, 70:190-220, 1992.
K. Racke, et al.; Effects of Cigarette Smoking or Ingestion of Nicotine on Platelet 5-hydroxytryptamine (5-HT) levels in smokers and non-smokers; The Clinical Investigator, 70: 201-204, 1992).
John D. Anczak, et al.; Tobacco Cessation in Primary Care: Maximizing Intervention Strategies; Clinical Medicine & Research; vol. 1, No. 3: 201-218, Jul. 2003.

* cited by examiner

*Primary Examiner*—Maureen M. Wallenhorst
(74) *Attorney, Agent, or Firm*—Sughrue Mion, PLLC

(57) ABSTRACT

A method for assessing nicotine dependence, which involves measuring a whole blood, serum or platelet-rich plasma serotonin level and rating the whole blood, serum or platelet-rich plasma serotonin level on such a scale that the higher it is, the higher nicotine dependence is.

8 Claims, 3 Drawing Sheets

METHOD FOR ASSESSING NICOTINE DEPENDENCE

The present invention relates to a method for assessing nicotine dependence. The method of the present invention reveals whether to use nicotine replacements such as nicotine gum to quit smoking.

Tobacco smoke contains carcinogens and mucosal irritants in large amounts. It is a well-known fact that habitual smoking is a risk factor for lung cancer and coronary diseases (G Howard et al., Cigarette smoking and progression of atherosclerosis. The atherosclerosis risk in community (ARIC) study., JAMA 279:119-124, 1998, and A K Hackshaw, M R Law, N J Wald, The accumulated evidence on lung cancer and environmental tobacco smoke., BMJ 1997;315:980-988 (18 October)). The fact indicates that smokers can live more healthily if they quit smoking. Many hospitals run smoking cessation clinics for outpatients to help smokers quit smoking. Smoking cessation clinics firstly assess a smoker's dependence on nicotine and provide smoking cessation programs using nicotine gum or nicotine patches as stop smoking aids.

Platelets are rich in serotonin, but they cannot synthesize it, but they store the serotonin contained in plasma through active uptake. Most of the plasma serotonin is synthesized by enterochromaffin cells intestine. It is reported that the amount of serotonin synthesized by enterochromaffin cells increases with the stimulation of nicotine in tobacco smoke (K Racke, H Schworer, Nicotine and muscarinic modulation of 5-hydroxytryptamine (5-HT) release from porcine and canine small intestine. The Clinical Investigator, 70:190-200,1992). It is reported that the serotonin level is higher in smokers than in nonsmokers (K. Racke, H Schworer, G Simon, Effects of cigarette smoking or ingestion of nicotine on platelet 5-hydroxytryptamine (5-HT) levels in smokers and non-smokers. The Clinical Investigator, 70:201-204, 1992).

It is actually difficult to assess nicotine dependence based on the blood nicotine level at which craving for smoking is induced. Therefore, at present, nicotine dependence tests based on total scores on questionnaires (such as the Fagerstrom nicotine dependence test) are used, and high scores are considered as high nicotine dependence. However, assessment by this type of nicotine dependence tests is quite subjective. Therefore, a more objective method for assessing nicotine dependence is demanded.

Although it seems likely that people with high nicotine dependence have high average blood nicotine levels, studies could not find any correlation between the level of its metabolite, cotinine, in the blood and nicotine dependence. This is probably because the blood cotinine level reflects the degree of smoking only within a short period before the measurement.

The present inventors thought that because nicotine damages vascular endothelial cells, the average blood nicotine level during a certain period might correlate with blood serotonin level which reflects the damage to vascular endothelial cells. As described above, nicotine stimulates enterochromaffin cells, and the production of serotonin by the cells increases. The present inventors thought if blood serotonin level fluctuates less sharply than blood cotinine level, blood serotonin level reflects the amount of smoking over a relatively long period, and that there might be a correlation between the average blood nicotine level over a certain period and blood serotonin level. As a result of their investigation, they have arrived at the present invention.

Namely, the present invention provides a method for assessing nicotine dependence, which comprises measuring a whole blood, serum or platelet-rich plasma serotonin level and rating the whole blood, serum or platelet-rich plasma serotonin level on such a scale that the higher it is, the higher nicotine dependence is. The present invention also provides a method for assessing nicotine dependence, which comprises measuring a whole blood, serum or platelet-rich plasma serotonin level, calculating the whole blood, serum or platelet-rich plasma serotonin level per unit platelet count from the whole blood, serum or platelet-rich plasma serotonin level, or measuring a serotonin level per unit platelet count, and rating the calculated whole blood, serum or platelet-rich plasma serotonin level per unit platelet count or the measured serotonin level per unit platelet count on such a scale that the higher it is, the higher nicotine dependence is. The present invention further provides a method for assessing change in nicotine dependence with time, which comprises assessing nicotine dependence using blood samples collected from the same individual at different times by either of the above-mentioned methods and comparing the assessments of nicotine dependence.

Figure 1:
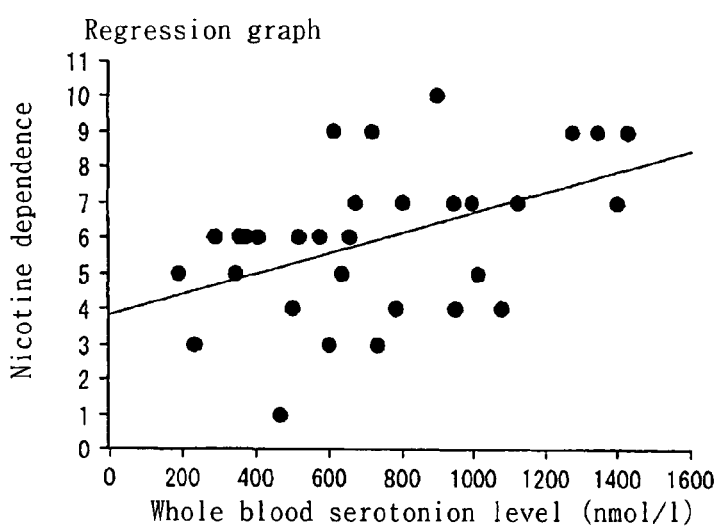
FIG. 1 shows the relation between the scores on a nicotine dependence test and whole blood serotonin level.

The present invention will be described in detail.

Blood contains hemocytes such as erythrocytes, leukocytes and platelets. Among them, platelets plentifully contain serotonin inside, while neither erythrocytes nor leukocytes contain it. Therefore, the total blood serotonin level is the sum of the serotonin present in the platelets and the plasma serotonin outside the platelets. The whole blood serotonin level may be measured using whole blood, which contains erythrocytes, leukocytes, platelets and plasma, as the sample. Serum may also be used as the sample, because platelets release serotonin into serum upon blood coagulation. Platelet-containing plasma obtained by centrifuging blood collected in blood collection tubes containing an anticoagulant at 450×g for about 5 minutes, called platelet-rich plasma, may also be used.

The method of the present invention requires measurement of the serotonin level in whole blood, serum or platelet-rich plasma. The measurement may be done by any method without any particular restrictions, for example, by liquid chromatography or immunoassay. For measurement of serotonin level by liquid chromatography, whole blood collected in a blood collection tube containing an anticoagulant is usually used as the sample after deproteinization. In immunoassay, a serum sample is used without pretreatment such as deproteinization. Measured values thus obtained have a good correlation with the nicotine dependence assessed by conventional methods based on scores of questionnaires such as the Fagerstrom tobacco dependence test, and a higher serotonin level in whole blood, serum or platelet-rich plasma is rated as higher nicotine dependence.

According to the method of the present invention, a good correlation was found between the whole blood, serum or platelet-rich plasma serotonin level per unit platelet count calculated from the whole blood, serum or platelet-rich plasma serotonin level or the serotonin level per unit platelet count and the nicotine dependence assessed by conventional tests. Namely, a higher whole blood, serum or platelet-rich plasma serotonin level per unit platelet count or a higher serotonin level per unit platelet count is rated as higher nicotine dependence.

The serotonin level per unit platelet count is calculated by measuring the serotonin level in a whole blood, serum or platelet-rich plasma sample and the serotonin level in plasma depleted of platelets (platelet-poor plasma) and dividing the difference between them by the separately measured platelet count. Because the serotonin level outside platelets is such a low level of 1% as compared with the platelet serotonin level, the whole blood, serum or platelet-rich plasma serotonin level per unit platelet count may be used instead of the serotonin level per unit platelet count. Therefore, in Examples, the whole blood serotonin level per unit platelet count obtained by dividing the whole blood serotonin level by the separately measured platelet count is discussed. The platelet count may be measured by any method, for example, by means of a commercial instrument, without particular restrictions.

Further, according to the present invention, the whole blood, serum or platelet-rich plasma serotonin level, the serotonin level per unit platelet count and the whole blood, serum or platelet-rich plasma serotonin level per unit platelet count calculated from the whole blood, serum or platelet-rich plasma serotonin level tend to be higher in those with high nicotine dependence than in nonsmokers (with no nicotine dependence). This indicates that it is possible to objectively assess nicotine dependence by comparing the whole blood, serum or platelet-rich plasma serotonin level, the serotonin level per unit platelet count or the whole blood, serum or platelet-rich plasma serotonin level per unit platelet count in an individual with the corresponding serotonin level in a nonsmoker and rating the serotonin level in the individual on such a scale that the more it exceeds the serotonin level in the nonsmoker, the higher the nicotine dependence is.

Further, the whole blood, serum or platelet-rich plasma serotonin level, the serotonin level per unit platelet count or the whole blood, serum or platelet-rich plasma serotonin level per unit platelet count were significantly lower in patients with treatment duration of 101 days or more than in new outpatients at a stop smoking clinic that includes both nicotine replacement therapies and non-nicotine therapies. This indicates that the whole blood, serum or platelet-rich plasma serotonin level, the serotonin level per unit platelet count or the whole blood, serum or platelet-rich plasma serotonin level per unit platelet count reflects reduction in nicotine dependence with the progress of the treatment given at the stop smoking clinic. The whole blood, serum or platelet-rich plasma serotonin level, the serotonin level per unit platelet count or the whole blood, serum or platelet-rich plasma serotonin level per unit platelet count in a patient at different times tends to decrease with the progress of treatment. Because the nicotine dependence of the patient decreases with the progress of treatment, it is possible to assess change in nicotine dependence with time by assessing nicotine dependence at different times based on the whole blood, serum or platelet-rich plasma serotonin level, the serotonin level per unit platelet count or the whole blood, serum or platelet-rich plasma serotonin level per unit platelet count and comparing the assessments of nicotine dependence.

The present invention provides a novel index for assessment of nicotine dependence and enables to assess nicotine dependence from the whole blood, serum or platelet-rich plasma serotonin level, the serotonin level per unit platelet count or the whole blood, serum or platelet-rich plasma serotonin level per unit platelet count calculated from the whole blood, serum or platelet-rich plasma serotonin level. It is possible to give a more objective assessment of nicotine dependence without a patient's subjectivity unlike the conventional tests.

EXAMPLES

Example 1

The nicotine dependence, blood serotonin levels, plasma serotonin levels, the ratios of blood/plasma serotonin, the serotonin levels per $10^7$ platelets, blood cotinine levels, oxidized LDL levels, triglyceride, cholesterol, HDL cholesterol, LDL cholesterol, platelet counts were measured in 31 outpatients at a smoking cessation clinic. The nicotine dependence was assessed by the Fagerstrom tobacco dependence test, the whole blood serotonin and plasma serotonin were measured as disclosed in JP-A-2002-277461. The blood cotinine levels were measured by gas chromatography mass spectrometer (GC/MS). The lipid analysis was done using the reagents manufactured by Kyowa Medex (HDL cholesterol; Determiner L HDL-C, LDL cholesterol; Determiner L LDL-C, cholesterol; Determiner TCII, triglyceride; Determiner TGII). Oxdized LDL was measured as disclosed in Itabe H. et al., J. Lipid Res., 37, 45-53 (1996). The platelet counts were measured with an automated hematology analyzer K-4000 (Sysmex Co.).

Nicotine dependence correlated with the whole blood serotonin levels and the serotonin levels per $10^7$ platelets, but did not correlate with the other items (with a significant difference, $p \geq 0.1$). The blood cotinine levels are shown for comparison.

Figure 2:
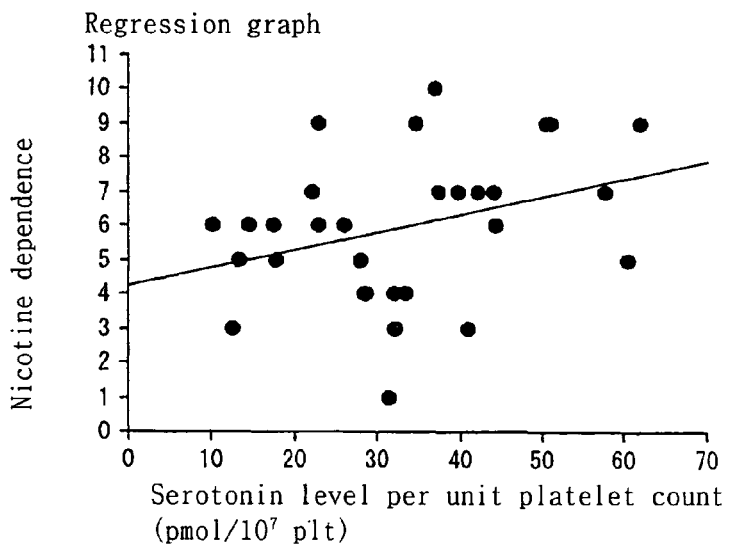
FIG. 2 shows the relation between the scores on a nicotine dependence test and serotonin level per unit platelet count.
Figure 3:
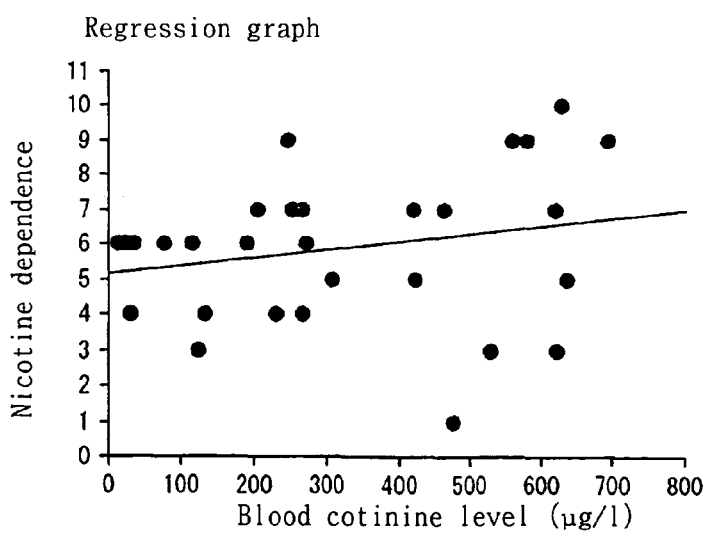
FIG. 3 shows the relation between the scores on a nicotine dependence test and blood cotinine level.

The results are shown in Table 1 and FIGS. 1 to 3. The scores on the nicotine dependence test showed a positive correlation with the whole blood serotonin levels with a good significance $p=0.0079$, and with the serotonin levels per $10^7$ platelets ($p=0.0663$). No correlation was found between the scores on the nicotine dependence test and the blood cotinine levels with a significance $p \geq 0.1$.

TABLE 1

Comparison with the scores on the nicotine dependence test (Y-axis)

| X-axis | Slope | Intercept | Squared correlation coefficient | p value |
|---|---|---|---|---|
| Whole blood serotonin level (nmol/l) | 0.003 | 3.834 | 0.219 | 0.0079 |
| Serotonin level per unit platelet count (pmol/$10^7$ plt) | 0.052 | 4.236 | 0.084 | 0.0663 |
| Blood cotinine level (µg/l) | 0.002 | 5.145 | 0.055 | 0.2227 |

Example 2

Figure 4:
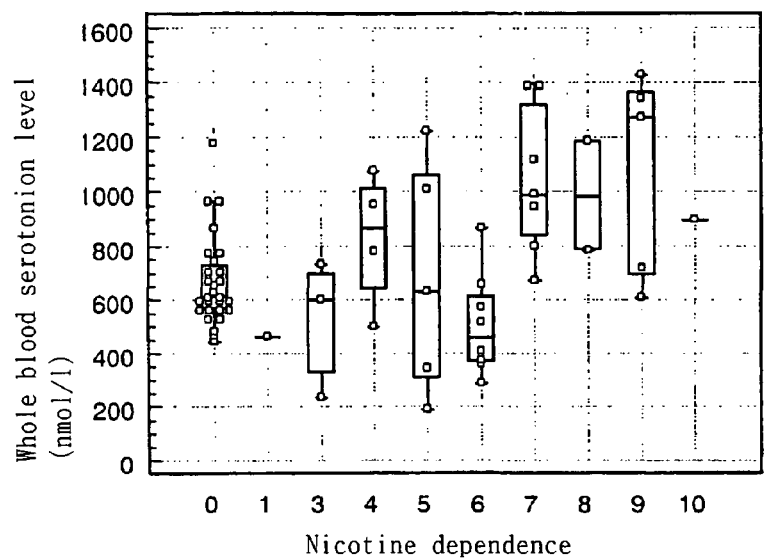
FIG. 4 shows the relation between the scores on a nicotine dependence test and whole blood serotonin level.

The nicotine dependence of 36 outpatients at a smoking cessation clinic was assessed by the Fagerstrom smoking dependence test, and the whole blood serotonin levels in the patients were measured. For comparison, the whole blood serotonin levels in healthy nonsmokers were measured. The nicotine dependence of the healthy nonsmokers was rated at 0. The results were analyzed to find a correlation between nicotine dependence and whole blood serotonin level. The results are shown in FIG. 4. The whole blood serotonin levels showed a tendency to increase with nicotine dependence. According to Spearman rank-correlation analysis, the correlation coefficient was 0.365 with a significant difference p=0.004 (P<0.05).

Figure 5:
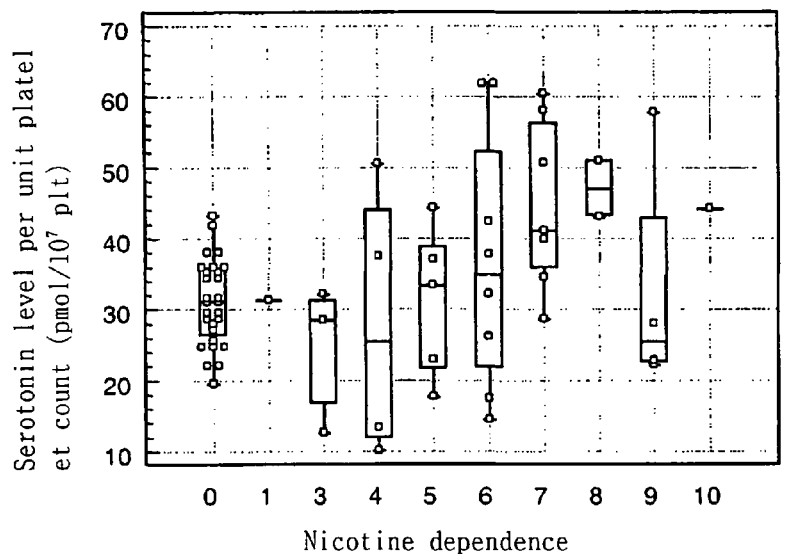
FIG. 5 shows the relation between scores on a nicotine dependence test and serotonin level per unit platelet count.

Separately, nicotine dependence of 35 outpatients at the smoking cessation clinic was assessed by the Fagerstrom tobacco dependence test. The whole blood serotonin levels and the platelet counts were measured, and the serotonin levels per $10^7$ platelets were calculated. For comparison, measurements were done with 28 healthy nonsmokers. The nicotine dependence of the healthy nonsmokers was rated at 0. The results were analyzed to fined a correlation between nicotine dependence and serotonin level per $10^7$ platelets. The results are shown in FIG. 5. The serotonin levels per $10^7$ platelets showed a tendency to increase with nicotine dependence. According to Spearman rank-correlation analysis, the correlation coefficient was 0.292 with a significant difference p=0.021 (P<0.05).

Example 3

Figure 6:
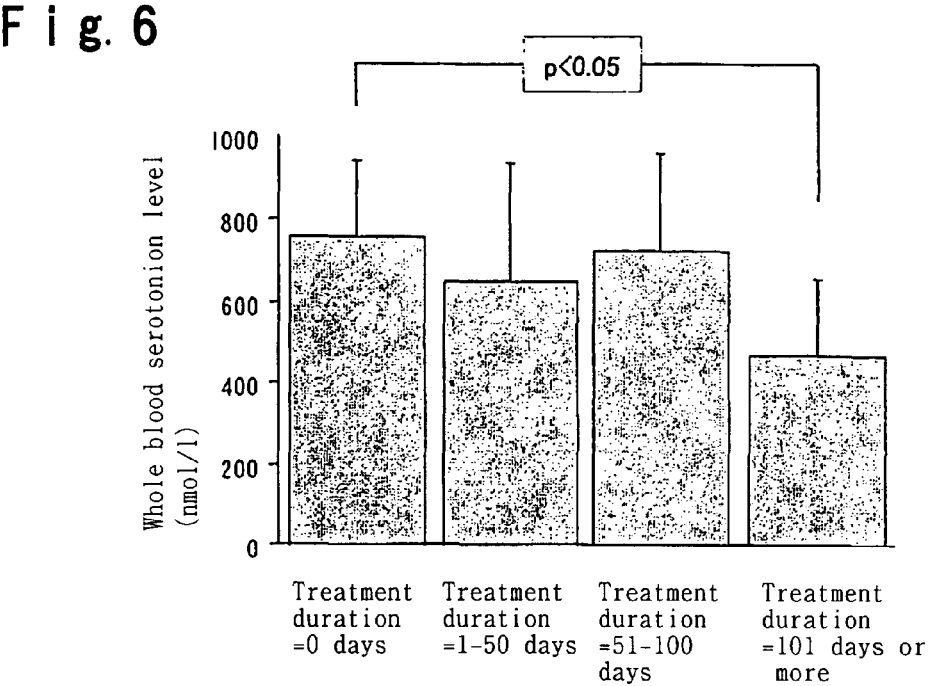
FIG. 6 shows the change in whole blood serotonin level during treatment.

The average whole blood serotonin levels were measured in 19 outpatients with treatment durations of 0 day, 7 outpatients with treatment durations of from 1 to 50 days, 8 outpatients with treatment durations of from 51 to 100 days and 7 outpatients with treatment durations of 101 days or more at a smoking cessation clinic, and the correlation between the duration of treatment and whole blood serotonin level was investigated. Some of the patients had used stop smoking aids, and the other had not. The results are shown in FIG. 6. There was no difference between the patients with treatment durations of from 1 to 50 days and the patients with treatment durations of from 51 to 100 days, but the serotonin levels were significantly lower in the patients with treatment durations of over 100 days than in the patients with treatment durations of 0 day in FIG. 6. This indicates that not only the average blood nicotine level and nicotine dependence but also the whole blood serotonin level decreased with the progress of the treatment. This indicates that measurement of whole blood serotonin level is effective in assessing nicotine dependence during treatment.

Figure 7:
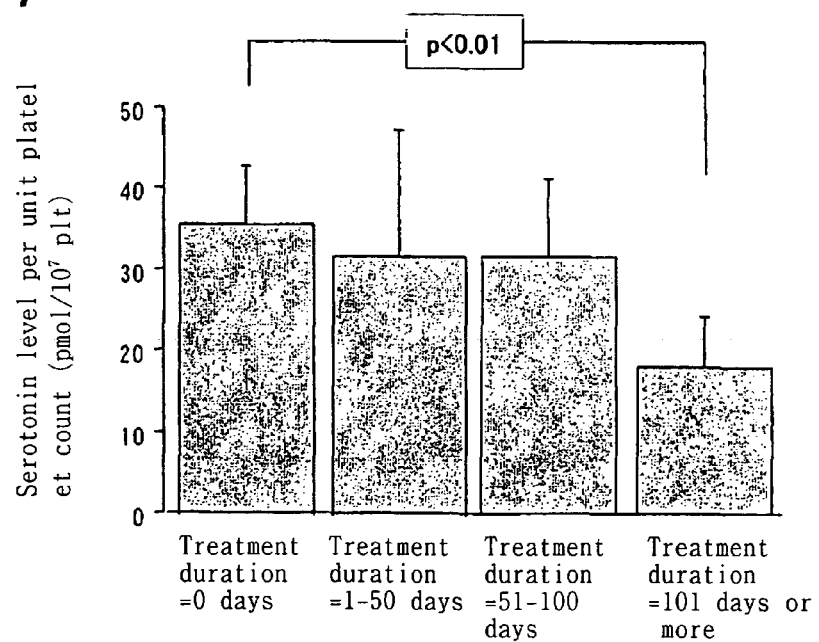
FIG. 7 shows the change in serotonin level per unit platelet count during treatment.

The average serotonin levels per $10^7$ platelet were measured in 18 outpatients with treatment durations of 0 day, 6 outpatients with treatment durations of from 1 to 50 days, 8 outpatients with treatment durations of from 51 to 100 days and 6 patients with treatment durations of 101 days or more at the smoking cessation clinic, and the correlation between the duration of treatment and the average serotonin level per $10^7$ platelet was investigated. The results are shown in FIG. 7. The serotonin levels per unit platelet count showed a tendency to decrease with the duration of treatment and significantly different in the patients with treatment durations of 0 day and in the patients with treatment durations of over 100 days in FIG. 7.

Example 4

The change in the whole blood serotonin levels and the blood serotonin levels per unit platelet count in three outpatients at a smoking cessation clinic was traced during treatment. The results are shown in Table 2. In patient A, both the whole blood serotonin level and the blood serotonin levels per unit platelet count decreased with the progress of the treatment. In patient B, both of them decreased during the first 56 days of the treatment, and then the whole blood serotonin level at the 90th day was similar to that at the 56th day, while the blood serotonin levels per platelet showed a further decrease. In patient C, both of them decreased with the progress of the treatment.

TABLE 2

Follow up of outpatients at smoking cessation clinic

| Patient | Duration (day) | Whole blood serotonin level | Serotonin level per unit platelet count (pmol/$10^7$ plt) |
|---|---|---|---|
| A | 0 | 784 | 43 |
|   | 15 | 770 | 48.2 |
|   | 113 | 755 | 31.7 |
|   | 143 | 281 | 12.6 |
| B | 0 | 1120 | 44.3 |
|   | 56 | 749 | 29.6 |
|   | 90 | 749 | 27.8 |
| C | 0 | 946 | 37.5 |
|   | 119 | 511 | 22.1 |
|   | 168 | 458 | 18.4 |

The entire disclosures of Japanese Patent Application No. 2003-365818 filed on Oct. 27, 2003 including specifications, claims, drawings and summaries are incorporated herein by reference in their entireties.

The invention claimed is:

1. A method for assessing nicotine dependence, which comprises measuring a whole blood, serum or platelet-rich plasma serotonin level in a smoker and rating the whole blood, serum or platelet-rich plasma serotonin level on such a scale that the higher it is, the higher nicotine dependence is, where said method further comprises assessing nicotine dependence in the smoker during treatment for smoking cessation at a clinic that includes both nicotine replacement therapies and non-nicotine therapies, and correlating the whole blood, serum or platelet-rich plasma serotonin level with the progression of the treatment for smoking cessation, wherein the whole blood, serum or platelet-rich plasma serotonin level is measured during the treatment for smoking cessation and the same decreases during the treatment to a desired level, thereby indicating the nicotine dependence of the patient decreases during the treatment, wherein nicotine dependence in the smoker is assessed using blood samples collected from the same smoker at different times with the progression in the treatment.

2. The method according to claim 1, further comprising comparing the whole blood, serum or platelet-rich plasma serotonin level in an individual that is the smoker with the whole blood, serum or platelet-rich plasma serotonin level in a nonsmoker and rating in the smoker the whole blood, serum or platelet-rich plasma serotonin level in the individual on such a scale that the more it exceeds the whole blood, serum or platelet-rich plasma serotonin level in the nonsmoker, the higher the nicotine dependence is.

3. A method for assessing change in nicotine dependence with time, which comprises assessing nicotine dependence using blood samples collected from the same individual that is the smoker at different times by the method as defined in claim 1 and comparing the assessments of nicotine dependence at different times throughout the smoker's treatment for smoking cessation.

4. The method according to claim 1, which method provides a good correlation with nicotine dependence as assessed by the Fagerstrom tobacco dependence test.

5. A method for assessing nicotine dependence, which comprises measuring a whole blood, serum or platelet-rich plasma serotonin level in a smoker, calculating the whole blood, serum or platelet-rich plasma serotonin level per unit platelet count from the whole blood, serum or platelet-rich plasma serotonin level in the smoker, or measuring a serotonin level per unit platelet count in the smoker, and rating the calculated whole blood, serum or platelet-rich plasma serotonin level per unit platelet count or the measured serotonin level per unit platelet count on such a scale that the higher it is, the higher nicotine dependence is, where said method further comprises assessing nicotine dependence in the smoker during treatment for smoking cessation at a clinic that includes both nicotine replacement therapies and non-nicotine therapies, and correlating the whole blood, serum or platelet-rich plasma serotonin level with the progression of the treatment for smoking cessation, wherein the whole blood, serum or platelet-rich plasma serotonin level is measured during the treatment for smoking cessation and the same decreases during the treatment, to a desired level, thereby indicating the nicotine dependence of the patient decreases during the treatment, wherein nicotine dependence in the smoker is assessed using blood samples collected from the same smoker at different times with the progression in the treatment.

6. The method according to claim 5 which comprises:
a) measuring the whole blood, serum or platelet-rich plasma serotonin level in an individual that is the smoker and calculating the whole blood, serum or platelet-rich plasma serotonin level per unit platelet count from it, or measuring the serotonin level per unit platelet count in the individual that is the smoker;
b) measuring the whole blood, serum or platelet-rich plasma serotonin level in a nonsmoker and calculating the whole blood, serum or platelet-rich plasma serotonin level per unit platelet count from it, or measuring the serotonin level per unit platelet count in the nonsmoker; and
c) rating in the smoker the whole blood, serum or platelet-rich plasma serotonin level per unit platelet count or the serotonin level per unit platelet count obtained in a) on such a scale that the more it exceeds the corresponding serotonin level per unit platelet count in the nonsmoker obtained in b), the higher the nicotine dependence is in the smoker.

7. A method for assessing change in nicotine dependence with time, which comprises assessing nicotine dependence using blood samples collected from the same individual that is the smoker at different times by the method as defined in claim 5 and comparing the assessments of nicotine dependence at different times throughout the smoker's treatment for smoking cessation.

8. The method according to claim 5, which method provides a good correlation with nicotine dependence as assessed by the Fagerstrom tobacco dependence test.

* * * * *